(12) United States Patent
Tsuboyama et al.

(10) Patent No.: US 7,459,559 B2
(45) Date of Patent: Dec. 2, 2008

(54) METAL COMPLEX AND ORGANIC LIGHT-EMITTING DEVICE

(75) Inventors: Akira Tsuboyama, Tokyo (JP); Kazunori Ueno, Ebina (JP); Masashi Hashimoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/755,049

(22) Filed: May 30, 2007

(65) Prior Publication Data

US 2007/0278939 A1 Dec. 6, 2007

(30) Foreign Application Priority Data

Jun. 2, 2006 (JP) .............................. 2006-154472
Apr. 27, 2007 (JP) .............................. 2007-118440

(51) Int. Cl.
*C07F 15/00* (2006.01)
*B32B 9/00* (2006.01)

(52) U.S. Cl. ........................... 546/2; 428/690; 428/917; 546/10

(58) Field of Classification Search ..................... 546/2, 546/10; 428/690, 917
See application file for complete search history.

(56) References Cited

U.S. PATENT DOCUMENTS

| | | | |
|---|---|---|---|
| 6,824,894 B2 | 11/2004 | Takiguchi et al. | 428/690 |
| 6,838,818 B2 | 1/2005 | Furugori et al. | 313/504 |
| 7,078,115 B2 | 7/2006 | Takiguchi et al. | 428/690 |
| 7,279,233 B2 | 9/2007 | Tsuboyama et al. | 428/690 |
| 2006/0094875 A1* | 5/2006 | Itoh et al. | 546/2 |
| 2006/0280968 A1 | 12/2006 | Kamatani et al. | 428/690 |
| 2007/0184302 A1 | 8/2007 | Iwawaki et al. | 428/690 |
| 2007/0207344 A1 | 9/2007 | Kamatani et al. | 428/690 |
| 2007/0228940 A1 | 10/2007 | Hashimoto et al. | 313/504 |

OTHER PUBLICATIONS

Wilkinson et al., "Synthesis and Luminescence of a Charge-Neutral, Cyclometalated Iridium (III) Complex Containing N∧C∧N- and C∧N∧C-Coordinating Terdentate Ligands," *Inorg. Chem.*, vol. 43, 6513-6515 (2004).

Lamansky et al., "Highly Phosphorescent Bis-Cyclometalated Iridium Complexes: Synthesis, Photophysical Characterization, and Use in Organic Light Emitting Diodes," *J. Am. Chem. Soc.*, vol. 123, 4304-4312 (2001).

Brooks et al., "Synthesis and Characterization of Phosphorescent Cyclometalated Platinum Complexes," *Inorg. Chem.*, vol. 41, 3055-3066 (2002).

Wiliams et al., "An Alternative Route to Highly Luminescent Platinum(II) Complexes: Cyclometalation with $N^\wedge C^\wedge N^\wedge$-Coordinating Dipyridylbenzene Ligands," *Inorg. Chem.*, vol. 42, 8609-8611, (2003).

* cited by examiner

*Primary Examiner*—Charanjit S Aulakh
(74) *Attorney, Agent, or Firm*—Fitzpatrick, Cella, Harper & Scinto (57) ABSTRACT

There are provided a light-emitting device which emits light stably with high efficiency, and a novel metal complex for realizing the light-emitting device. The novel metal complex has terdentate coordination.

3 Claims, 6 Drawing Sheets

CBP

Bphen

PVK

METAL COMPLEX AND ORGANIC LIGHT-EMITTING DEVICE

BACKGROUND OF THE INVENTION

1. Field of the Invention

The present invention relates to a novel metal complex and an organic light-emitting device including the same.

2. Description of the Related Art

There have been vigorously conducted developments of light-emitting materials with a view to provide an organic light-emitting device (LED) which emits light stably with high efficiency. In particular, developments of phosphorescent light-emitting materials have strenuously been conducted because phosphorescent light-emitting devices utilizing phosphorescence can emit light with high efficiency. There have been conducted developments of cyclometalated iridium complexes using a cyclometalated bidentate ligand (C—N) of Ir(C—N)$_3$ and (C—N)$_2$IrAcac types and cyclometalated platinum complexes (see, "Highly Phosphorescent Bis-Cyclometalated Iridium Complexes: Synthesis, Photophysical Characterization, and Use in Organic Light Emitting Diodes", Lamansky, S.; Djurovich, P.; Murphy, D.; Abdel-Razzaq, F.; Lee, H.-E.; Adachi, C.; Burrows, P. E.; Forrest, S. R.; Thompson, M. E., J. Am. Chem. Soc.; 2001; 123(18); 4304-4312, and "Synthesis and Characterization of Phosphorescent Cyclometalated Platinum Complexes", Brooks, J.; Babayan, Y.; Lamansky, S.; Djurovich, P, I.; Tsyba, I.; Bau, R.; Thompson, M. E., Inorg. Chem.; 2002; 41(12); 3055-3066).

Recently, there have been reported an iridium complex and a platinum complex using a cyclometalated terdentate ligand (see, "Synthesis and Luminescence of a Charge-Neutral, Cyclometalated Iridium (III) Complex Containing N^C^N- and C^N^C-Coordinating Terdentate Ligands", Wilkinson, A. J.; Goeta, A. E.; Foster, C. E.; Williams, J. A. G., Inorg. Chem.; 2004; 43(21); 6513-6515, and "An Alternative Route to Highly Luminescent Platinum (II) Complexes: Cyclometalation with N^C^N-Coordinating Dipyridylbenzene Ligands", J. A. Gareth Williams, Andrew Beeby, E. Stephen Davies, Julia A. Weinstein, and Claire Wilson, Inorg. Chem.; 2003; 42(26) pp 8609-8611). The iridium complex disclosed in "Synthesis and Luminescence of a Charge-Neutral, Cyclometalated Iridium (III) Complex Containing N^C^N- and C^N^C-Coordinating Terdentate Ligands" above has low stability and is particularly unsuitable as a light-emitting material because the iridium complex is decomposed in an excited state upon PL measurement for observing light emission when irradiated with light. Meanwhile, the platinum complex disclosed in "An Alternative Route to Highly Luminescent Platinum (II) Complexes: Cyclometalation with N^C^N-Coordinating Dipyridylbenzene Ligands" above has relatively high stability and a high emission quantum yield and is therefore suitable as a light-emitting material. However, according to the report, synthesis of the complex requires a step of refluxing for 3 days, so that there has been a problem in manufacturing that the step of synthesizing a complex takes an extremely long period of time. In addition, there has been a technical problem that the degree of freedom of selection of emission colors of the phosphorescent materials is low, so that there has not been particularly obtained a phosphorescent material of blue color emission with good performance.

SUMMARY OF THE INVENTION

The present invention provides a light-emitting device which emits light stably with high efficiency and a novel metal complex for realizing the light-emitting device.

According to the present invention, there is provided a metal complex having a partial structure represented by the following formula (1):

(1)

wherein, M is Ir or Pt; at least two of $R_1$, $R_2$, and $R_3$ are each a fluorine atom; A is selected from a pyridine ring, a quinoline ring, and an isoquinoline ring each having a nitrogen atom as a coordinating atom; and A may have a substitutent selected from an alkyl group and an alkoxyl group each having 4 or less carbon atoms.

According to the present invention, there can be provided a light-emitting device which emits light stably with high efficiency and a novel metal complex for realizing the light-emitting device.

Further features of the present invention will become apparent from the following description of exemplary embodiments with reference to the attached drawings.

DESCRIPTION OF THE EMBODIMENTS

The metal complex according to the present invention has a partial structure represented by the following formula (1):

(1)

wherein, M is Ir or Pt; at least two of $R_1$, $R_2$, and $R_3$ are each a fluorine atom; A is selected from a pyridine ring, a quinoline ring, and an isoquinoline ring each having a nitrogen atom as a ligand atom; and A may have a substitutent selected from an alkyl group and an alkoxyl group each having 4 or less carbon atoms.

In addition, the metal complex having the partial structure represented by the formula (1) is preferably a metal complex having a partial structure represented by the following formula (2):

(2)

In addition, the metal complex having the partial structure represented by the formula (1) is preferably a metal complex having a partial structure represented by the following formula (3):

(3)

According to the present invention, there is also provided an organic light-emitting device including an anode, a cathode, and an organic compound layer interposed between the anode and the cathode, wherein the organic compound layer includes the metal complex having the partial structure represented by the formula (1).

In addition, the organic light-emitting device preferably has an emission peak wavelength of 500 nm or less.

Figure 1:
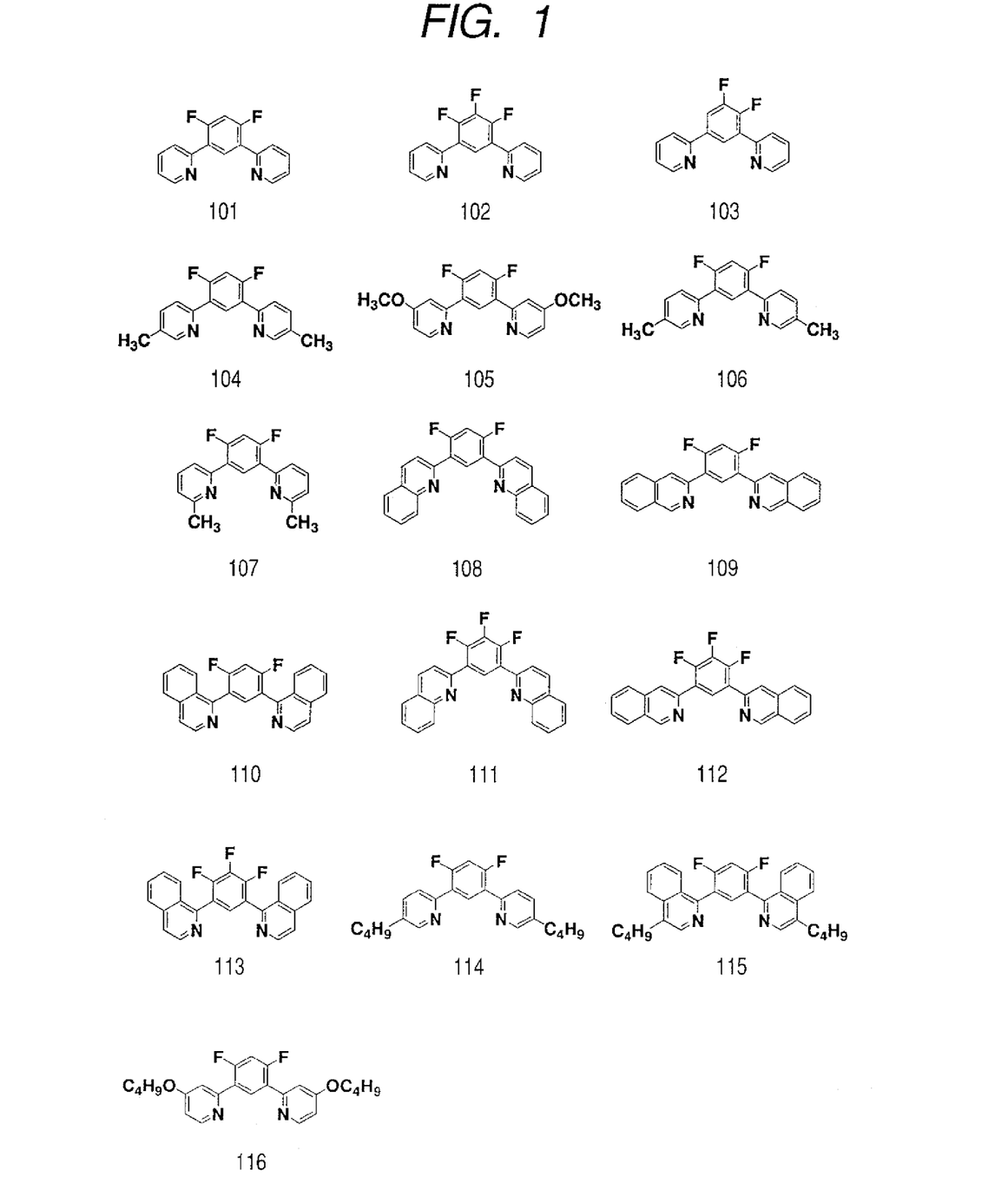
FIG. 1 illustrates examples of ligands which can be used in the present invention.
Figure 2:
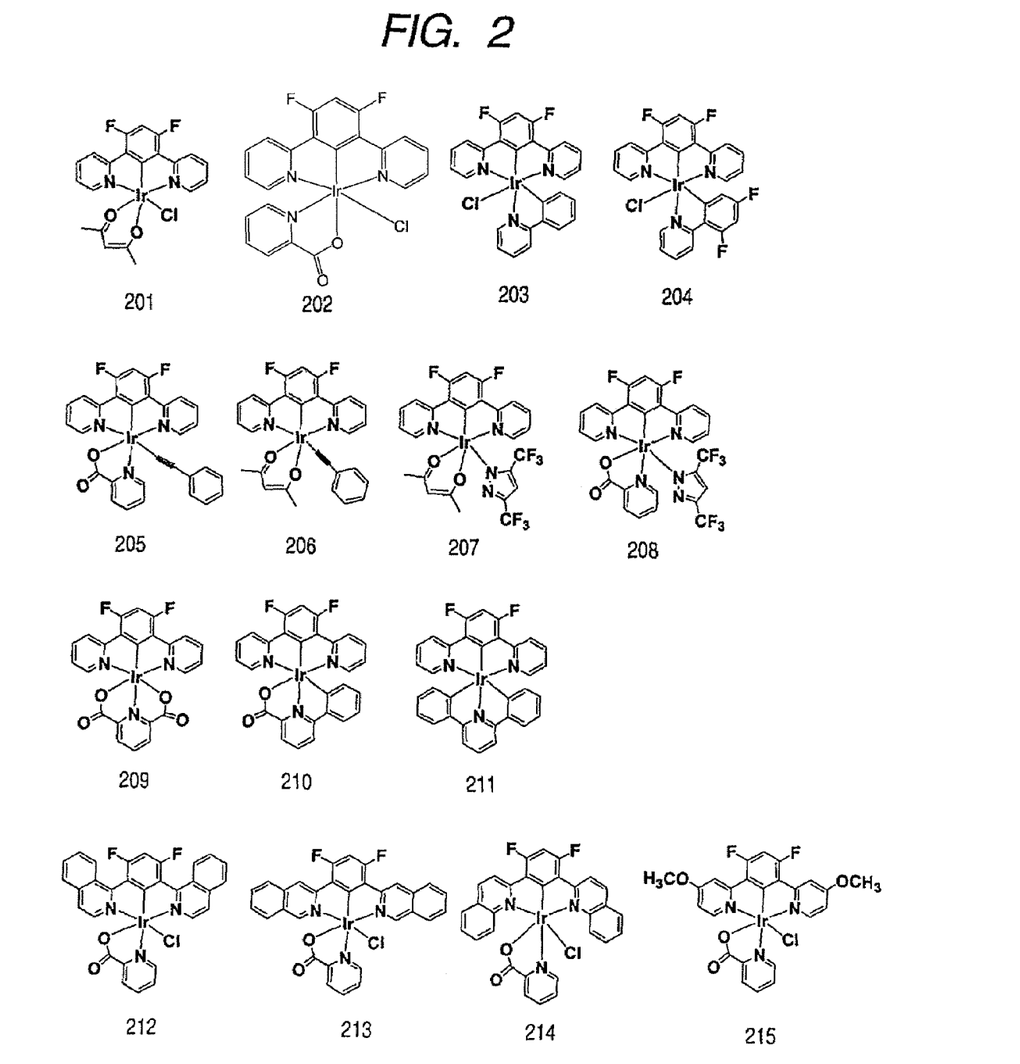
FIG. 2 illustrates iridium complexes as examples of the metal complex of the present invention.

The present invention will be described in further detail by referring to the drawings. FIG. 1 illustrates examples of ligands which can be used in the present invention. At least 2 hydrogen atoms of each of phenyl groups of the ligands are each substituted by a fluorine atom. FIG. 1 illustrates examples of ligands in each of which a phenyl group is bonded to a heterocycle such as a pyridine ring, an isoquinoline ring, or a quinoline ring. Those ligands each have a ligand atom of nitrogen. FIG. 2 illustrates iridium complexes as examples of the light-emitting metal complex of the present invention.

Figure 3:
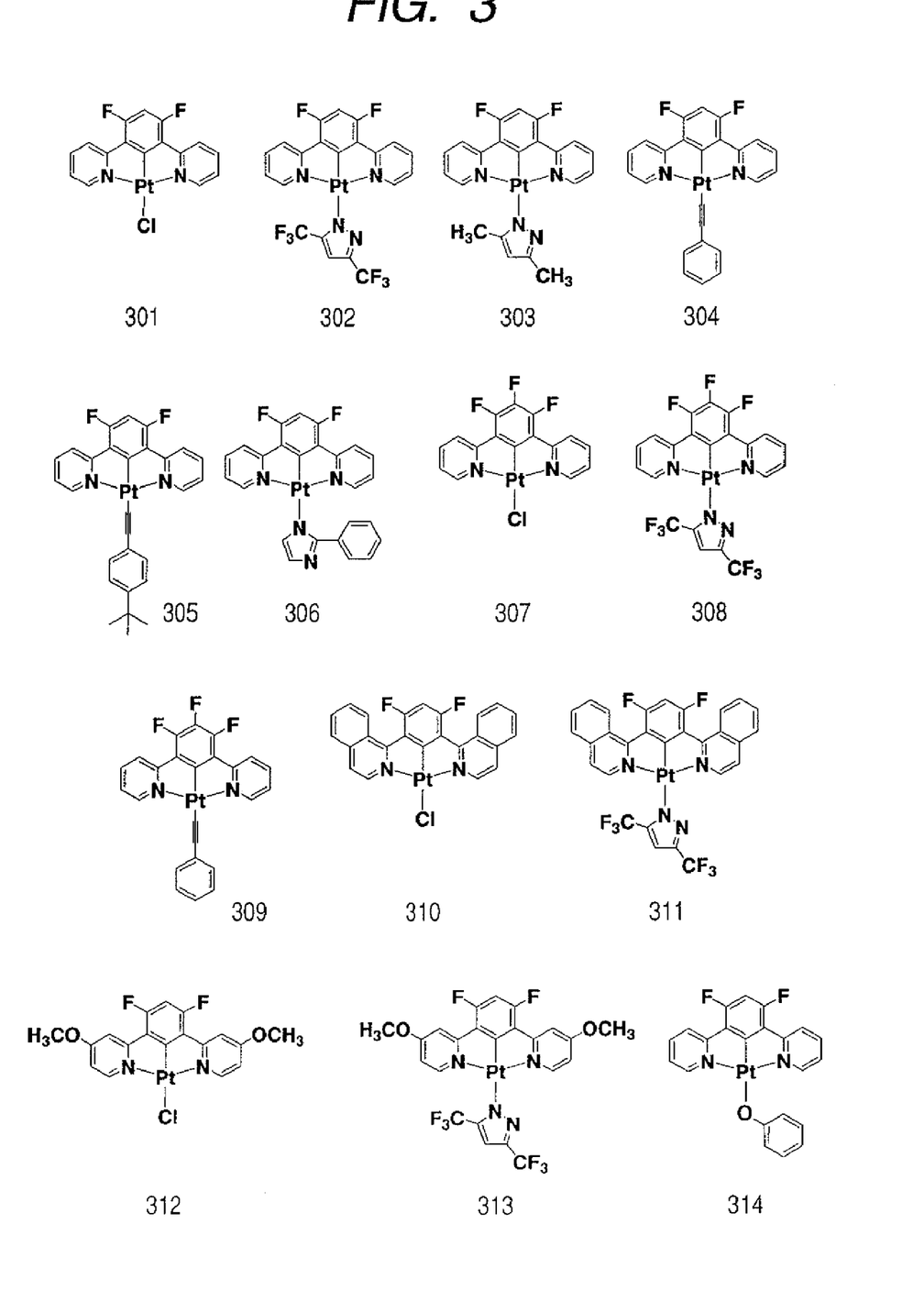
FIG. 3 illustrates examples of the platinum complex of the present invention.

In addition, FIG. 3 illustrates examples of the platinum complex of the present invention.

Unlike the conventional complexes, the following effects can be expected by using the ligand having a substitutent including a fluorine atom. In particular, use of a ligand in which at least two of the phenyl groups are substituted by fluorine can provide various advantages due to the fluorine atom as described below.

(1) The electron-withdrawing property of the fluorine atom changes emission wavelength to widen the design range of emission color.

(2) The fluorine atom causes a decrease in sublimation temperature, which facilitates production of a device in a case where vacuum deposition is used.

(3) The fluorine atom increases the solubility to typical organic solvents, which facilitates purification and production of a device by a method using a solvent, such as spin coating or a printing method.

(4) The electron-withdrawing property of the fluorine atom promotes a cyclometalation reaction, which shortens a period of time required for the synthesis reaction and improves productivity.

(5) The fluorine atom weakens molecular interaction to suppress concentration quenching.

Regarding the above-mentioned item (1), when an electron-withdrawing group is introduced into a phenyl group, HOMO mainly distributed in the phenyl group and a central metal is stabilized, whereby an emission energy shifts to a higher energy level (shorter wavelength). In the complex of the present invention, the emission color shifts to blue color as compared to that of a complex using an unsubstituted ligand as a basis. As a result, the color adjustment becomes possible, and in particular, application to blue light emission with a high efficiency is expected. For controlling the emission wavelength, an auxiliary ligand also plays an important role. To shift the light emission to a higher energy level (shift to shorter wavelength), it is desirable to select a ligand having a strong ligand field. For example, of the ligands used in the exemplified compounds illustrated in FIG. 3, the relative relationship between the strengths of the ligand fields is such that chlorine atom (301)<pyrazole group (302, 303, 308) <ethynyl group (304, 305), and in order to shift the emission spectrum to a higher energy level, a pyrazole group and an ethynyl group are desirably used.

Regarding the above-mentioned item (4), the reason why progression of the cyclometalation reaction is facilitated by the introduction of the fluorine group is considered as follows. In a case of a reaction in which hydrogen is withdrawn from the phenyl group and a metal is coordinated, the acidity of the hydrogen atom on carbon to which the metal is bonded is increased by the electron-withdrawing effect of the fluorine group, resulting in facilitation of dissociation of the hydrogen atom. Therefore, formation of a bond between the metal atom and the carbon atom proceeds rapidly.

As described above, the metal complex of the present invention has various characteristics improved as compared with unsubstituted metal complexes or metal complexes having a fluorine-based substitutent.

EXAMPLES

Example 1

In this example, synthesis of the platinum complex 301 (FIG. 3) using the ligand 101 illustrated in FIG. 1 is described. A reaction scheme for the formation of the ligand 101 is shown below.

11.6 mg (60 mmol) of 1-bromo-2,4-difluorobenzene (A001) (manufactured by Tokyo Chemical Industry Co., Ltd.) and 200 mg of reduced iron were placed in a 50-mL two-necked flask. A condenser was mounted on one of the two necks of the flask, and another neck was sealed with a septum. The liquid mixture was heated to 60° C., and 9,890 mg (60 mmol) of $Br_2$ was added dropwise to the liquid mixture with an injection syringe for 30 minutes, followed by heating at 60° C. for 2 hours. The resultant solution was cooled to room temperature and was then added to an aqueous 10% NaOH solution. The mixture was added with toluene and the organic layer was extracted twice, followed by drying with magnesium sulfate. The resultant solution was subjected to filtration to remove magnesium sulfate, and was then concentrated to give 13.9 g of a mixture of toluene and 1,3-dibromo-4,6-difluorobenzene (A002) in a ratio of 30% : 70%.

Next, in order to obtain the ligand 101, 1,3-dibromo-4,6-difluorobenzene (A002) as a raw material was reacted with trimethyl(2-pyridyl)tin. 20 cc of toluene, 544 mg (2 mmol) of A002, 1,452 mg (6 mmol) of trimethyl(2-pyridyl)tin, 140 mg (0.2 mmol) of $Pd(PPh_3)_2Cl_2$, and 20 mmol (20 mmol) of LiCl were placed in a two-necked flask, and the whole was refluxed for 3 hours. The mixture was cooled to room temperature and was added with chloroform to dissolve needle crystals. The solution was subjected to filtration to remove black substances. After concentration, the resultant was added with toluene for dissolution, and recrystallization was performed in a refrigerator at −20° C. to give 420 mg of a white crystal (ligand 101) (yield=77%).

The platinum complex 301 was obtained by refluxing the ligand 101 (27 mg, 0.1 mmol) and $K_2PtCl_4$ (42 mg, 0.1 mmol) in acetic acid (5 cc). The mixture was cooled to room temperature and was allowed to stand, whereby an orange needle crystal was precipitated. The precipitated crystal was filtered off and washed with water and then with $CH_3OH$ to give 35 mg of the platinum complex 301 (yield=47%).

Figure 4:
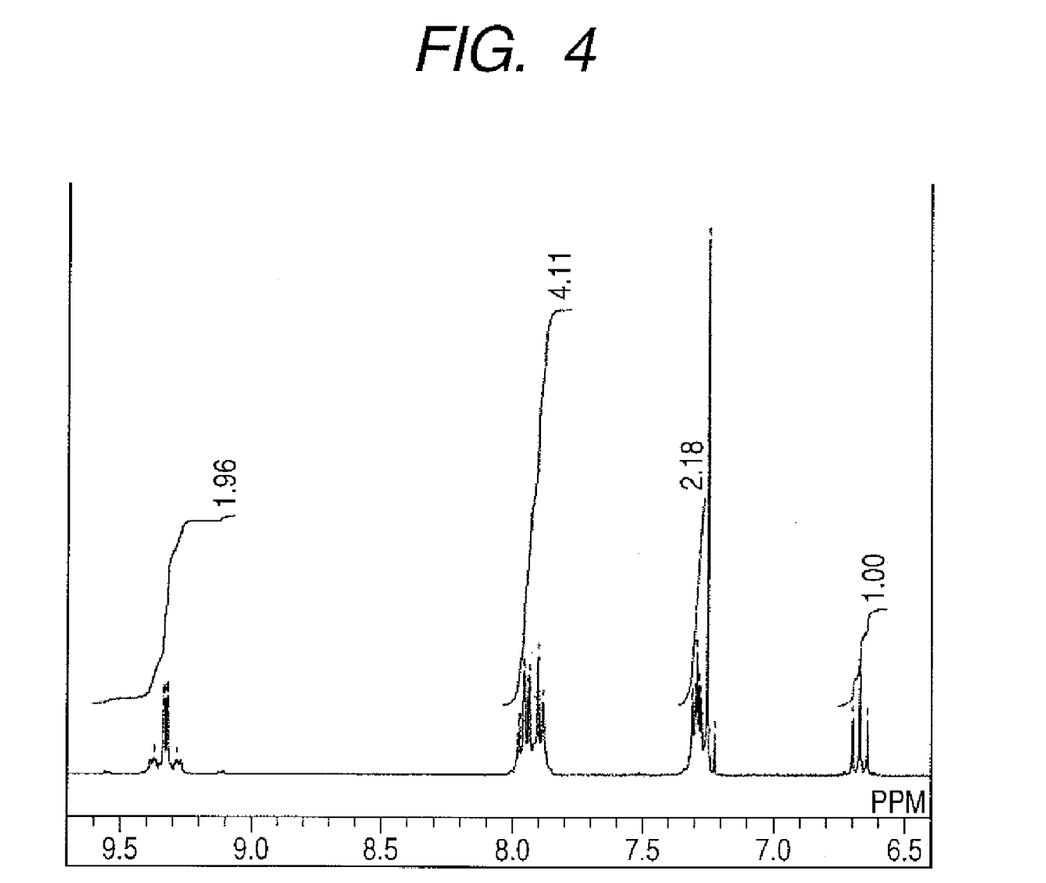
FIG. 4 is a proton NMR chart.

FIG. 4 is a proton NMR chart used for identification. The resultant compound was confirmed to have $M^+$ of 497.0 by Matrix Assisted Laser Desorption/Ionization Time of Flight Mass Spectrometry (MALDI-TOFMS) using Autoflex (trade name; manufactured by Bruker Daltonics).

Figure 5A:
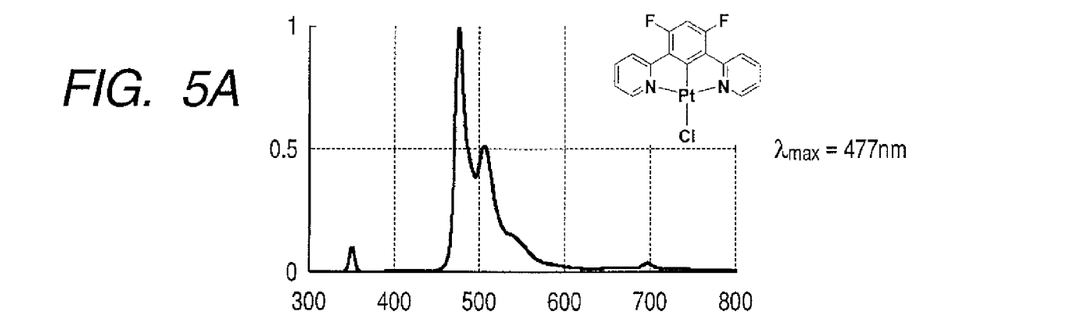
FIGS. 5A, 5B, and 5C are graphical representations illustrating emission spectra of metal complexes.

An emission spectrum of the platinum complex 301 is shown in FIG. 5A, as compared to those of compounds of other examples. The platinum complex 301 of this example was found to have an emission peak wavelength of 476 nm which was significantly shorter than that of a known material of a complex having methyl substitutents, and to emit blue light. In addition, it was found that the platinum complex had an emission quantum yield in a toluene solution of 50%, and thus was a light-emitting material which emits light with a high efficiency. In addition, it took 3 days to produce a complex of the ligand having methyl groups or the like (see, "An Alternative Route to Highly Luminescent Platinum (II) Complexes: Cyclometalation with N^C^N-Coordinating Dipyridylbenzene Ligands" above), while the reaction in this example was completed in 3 hours. The reaction of the ligand of this example rapidly proceeded, thereby showing a higher productivity than a complex having the ligand containing no fluorine atom.

Example 2

A complex 302 was synthesized by using as a starting material the complex 301 synthesized in Example 1.

First, 3,5-bis(trifluoromethyl)pyrazole and 1.2 equivalents of NaH were stirred in THF at room temperature to prepare sodium 3,5-bis(trifluoromethyl)pyrazolate. A toluene dispersion solution of the complex 301 (25 mg) was added with 1.5 equivalents of sodium 3,5-bis(trifluoromethyl)pyrazolate. When the mixture was stirred at room temperature for about 10 minutes, the undissolved complex 301 was eliminated, which indicated that the reaction rapidly progressed. The mixture was heated to 100° C. and stirred for 2 hours, and was then cooled to room temperature, followed by concentration.

Figure 5B:
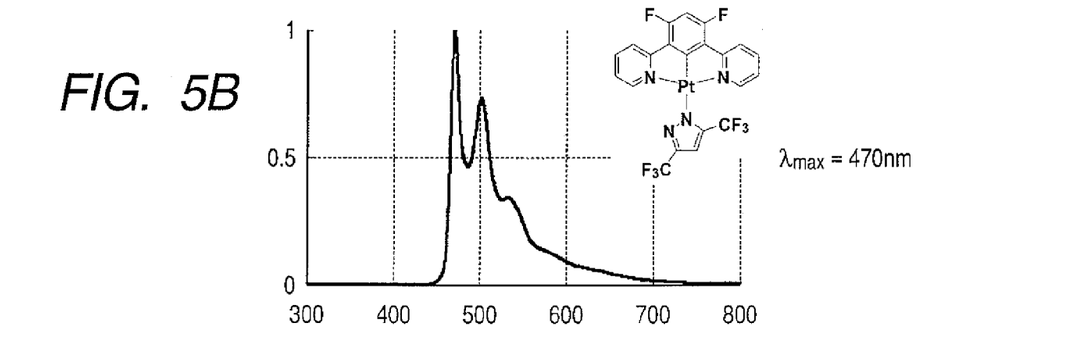

The resultant mixture was added with and dissolved in acetone, concentrated, and cooled at −20° C. overnight for recrystallization to give a yellow crystal. The resultant compound was observed to have $M^+$ of 665.0 by MALDI-TOFMS. An emission spectrum of the platinum complex 302 is shown in FIG. 5B, as compared to those of compounds of other examples. In addition, the emission quantum yield in a toluene solution was 60%, and thus the platinum complex 302 was found to be a light-emitting material which emitted light of a shorter wavelength with a higher efficiency than the complex 301.

Example 3

Descriptions are made of a synthesis method for an iridium complex 202 having a ligand 101, and the physical properties thereof.

202

The ligand 101 (1 mmol, 268 mg) and IrCl$_3$·3H$_2$O (1 mmol, 353 mg) were added to 10 cc of ethoxyethanol, and the whole was stirred at 90° C. for 5 hours. After the mixture was cooled to room temperature, a precipitated yellow solid was collected by filtration, washed with water and ethanol, and dried under vacuum at 80° C. to give A004 (440 mg, yield=83%). Next, A004 (53 mg, 0.05 mmol), picolinic acid (18 mg, 0.15 mmol), and Na$_2$CO$_3$ (64 mg, 0.6 mmol) were added to 10 cc of ethoxyethanol, and the whole was heated to reflux for 6 hours. After being cooled to room temperature, the mixture was concentrated and added with water. A yellow solid was collected by filtration. The solid was dissolved in a 1:1 solution of chloroform/heptane, and the whole was cooled to −20° C., followed by collection of a recrystallized yellow crystal by filtration.

Figure 5C:
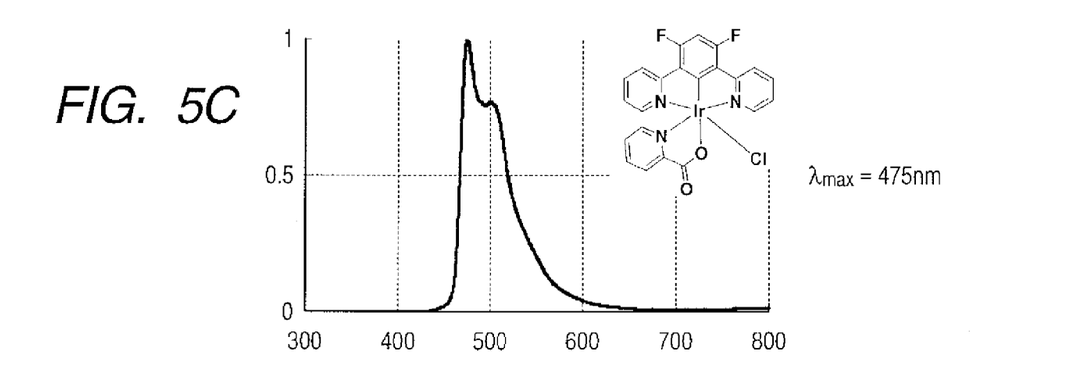

The resultant compound was observed to have $M^+$ of 617.0 by MALDI-TOFMS. An emission spectrum of the iridium complex 202 is shown in FIG. 5C, as compared to those of the compounds of other examples. The complex had substantially the same emission peak wavelength as that of the complex 301 of Example 1.

Examples 4 and 5

The platinum complexes 301 and 302 synthesized, respectively, in Examples 1 and 2 were used as light-emitting materials. In the present examples, a device having a device constitution of 3 organic layers was used. ITO (anode) was patterned in a thickness of 100 nm onto a glass substrate (substrate 607) such that the opposing electrode area was 3 mm$^2$. The below-mentioned organic layers and electrode layer were continuously formed onto the ITO substrate through vacuum deposition by resistive heating in a vacuum chamber at 10$^{-4}$ Pa.

Figure 6:
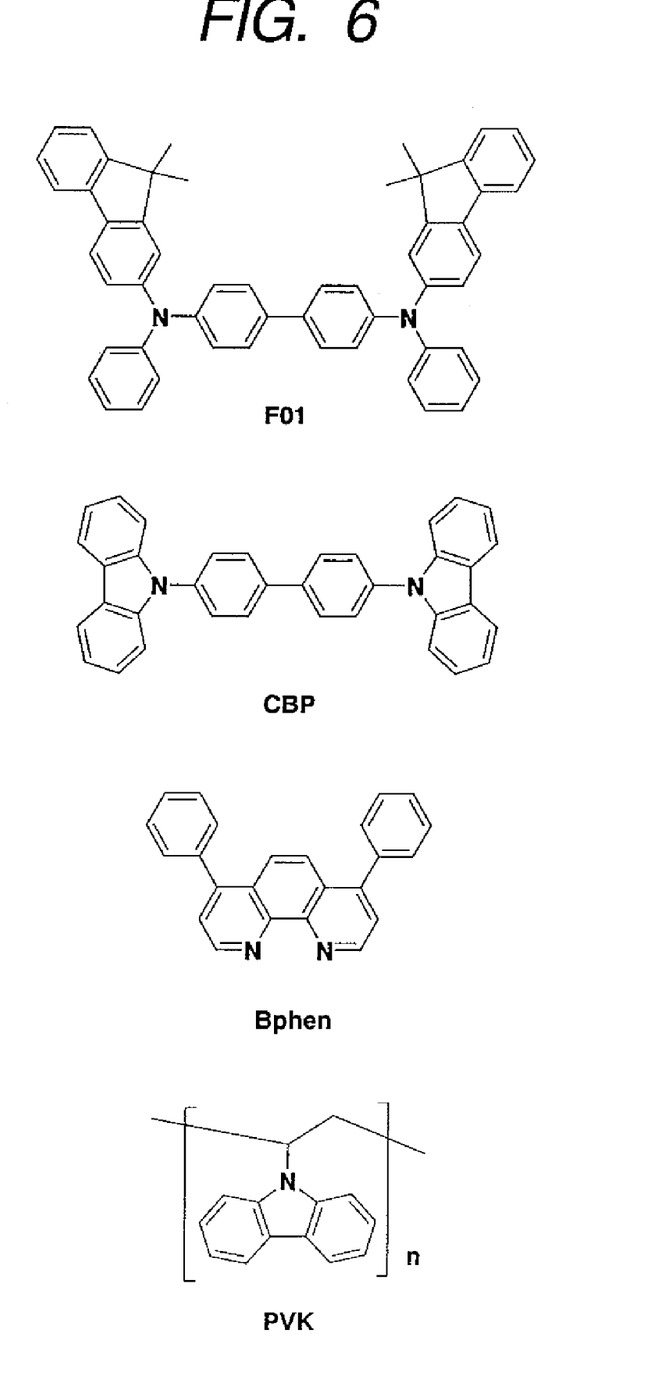
FIG. 6 illustrates structural formulae of organic compounds which are used in Examples of the present invention.

FIG. 6 illustrates structural formulae and abbreviations of the organic compounds used in the examples. The device constitution was as follows: ITO/F01 (30 nm)/CBP: light-emitting material [10 wt %] (40 nm)/Bphen (30 nm)/Cs$_2$CO$_3$ (5 nm)/Al.

A DC voltage was applied to the device with the anode (ITO) being used as a positive electrode and the cathode (Al) being used as a negative electrode to evaluate the device characteristics. The emission intensity was measured by using spectrometers SR1 and BM7 (trade names; manufactured by Topcon Corporation). The current value at the time of voltage application was measured by using 4140Bd (trade name; manufactured by Hewlett-Packard Company).

As a result, EL light emission with a high efficiency was measured for each of the devices as shown in Table 1 below at a luminance of 300 cd/m$^2$. As for emission spectra, substantially the same emission spectra as those illustrated in FIGS. 5A and 5B were observed, respectively, whereby it was confirmed that the light emission was derived from the complexes. The complex of the present invention was found to be effective for a light-emitting dopant of an organic EL device. In addition, the EL light emission was stable even after lighting for 3 hours, so that the stability of the light emission was found to be satisfactory.

TABLE 1

|  |  | Emission peak wavelength | cd/A | lm/W |
|---|---|---|---|---|
| Example 4 | Complex 301 | 480 nm | 5.6 | 4.3 |
| Example 5 | Complex 302 | 475 nm | 7.8 | 7.2 |

Example 6

In Example 6, the platinum complex 302 was used as a light-emitting dopant and PVK (see FIG. 6) as a high-molecular EL material was used as a host material.

The device constitution was as follows: ITO/PEDOT:PSS (30 nm)/PVK+light-emitting material (platinum complex 302) (80 nm)/Cs$_2$CO$_3$ (3 nm)/Al.

As PEDOT:PSS, Baytron P AI 4083 (trade name; manufactured by H. C. Stark) was used and subjected to spin coating at 4,000 rpm to form a thin film of 30 nm in thickness. As PVK, one manufactured by Sigma-Aldrich Corporation was used, and o-dichlorobenzene was used as a solvent. 0.9 wt. % of PVK and 0.1 wt. % of the platinum complex 302 were dissolved in O-dichlorobenzene with heating and stirring, and the solution subjected to spin coating at 2,000 rpm. The resultant layer was dried at 80° C. in a nitrogen atmosphere, and Cs$_2$CO$_3$ was formed into a film as an electron injection layer by vacuum deposition and Al was vapor deposited in a thickness of 100 nm thereon.

The thus obtained device was evaluated for EL light emission characteristics thereof. As a result, EL light emission with a high efficiency was measured as shown in Table 2 at a luminance of 300 cd/m$^2$. As for emission spectrum, substantially the same emission spectrum as that illustrated in FIG. 5B was observed, whereby it was confirmed that the light emission was derived from the complex. The complex of the present invention was found to be effective for a light-emitting dopant of an organic EL device. In addition, the EL light emission was stable even after lighting for 3 hours, so that the stability of the light emission was found to be satisfactory.

TABLE 2

|  |  | Emission peak wavelength | cd/A | lm/W |
|---|---|---|---|---|
| Example 6 | Complex 302 | 475 nm | 2.4 | 4.2 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2006-154472, filed on Jun. 2, 2006, and 2007-118440, filed on Apr. 27, 2007, which are hereby incorporated by reference herein in their entirety.

What is claimed is:

1. A metal complex represented by any one of the following formulae:

2. An organic light-emitting device, comprising:
    an anode;
    a cathode; and
    an organic compound layer interposed between the anode and the cathode,
    wherein the organic compound layer comprises the metal complex set forth in claim 1.

3. The organic light-emitting device according to claim 2, which has an emission peak wavelength of 500 nm or less.

* * * * *